United States Patent [19]

Kizawa et al.

[11] Patent Number: 5,447,856
[45] Date of Patent: Sep. 5, 1995

[54] METHOD FOR THE PRODUCTION OF TREHALOSE USING STRAINS OF MICROCOCCUS AND DEINOCOCCUS

[75] Inventors: Hideki Kizawa, Tsukuba; Kenichiro Miyagawa, Toyono; Yukihiro Kanegae, Kobe; Yoshio Sugiyama, Takasago, all of Japan

[73] Assignee: Takeda Chemical Industries, Ltd., Osaka, Japan

[21] Appl. No.: 208,312

[22] Filed: Mar. 10, 1994

[30] Foreign Application Priority Data

Mar. 18, 1993 [JP] Japan .................. 5-058269
Feb. 21, 1994 [JP] Japan .................. 6-022768

[51] Int. Cl.$^6$ .................. C12P 19/12; C12P 1/04; C07H 3/04
[52] U.S. Cl. .................. 435/100; 435/170; 435/859; 536/123.13; 536/124
[58] Field of Search .................. 435/100, 170, 859; 536/123.13, 124, 127

[56] References Cited

U.S. PATENT DOCUMENTS 3,655,512 4/1972 Tanaka et al. .................. 435/100
5,169,767 12/1992 Matsuura et al. .................. 435/100

FOREIGN PATENT DOCUMENTS

0555540A1 8/1993 European Pat. Off. .
50-154485 12/1975 Japan .

OTHER PUBLICATIONS

Bergey's Manual of Systematic Bacteriology, vol. 2, (1986), pp. 1288–1289, 1301.
The extracellular Accumulation of Trehalose and Glucose, [Agr. Biol. Chem. vol. 33, No. 2, pp. 190–195, 1969].
Short Communication, Journal of General Microbiology (1980), 121, 483–486.

*Primary Examiner*—David M. Naff
*Assistant Examiner*—Francisco C. Prats
*Attorney, Agent, or Firm*—Foley & Lardner

[57] ABSTRACT

A microorganism belonging to the Gram-positive cocci having not less than about 55 mol % of guanine plus cytosine content of DNA is cultivated in a medium. Trehalose is produced and extracellularly accumulated in the medium with a good yield. The present method, therefore, brings about a feasible method for the industrial production of trehalose. Preferably, the microorganism used is *Deinococcus proteolyticus* (IFO 15345), *Deinococcus erythromyxa* (IFO 15344), *Deinococcus radiopugnans* (IFO 15348), *Micrococcus varians* (FERM BP-4238 and IFO 3765), *Micrococcus agilis* (IFO 15323) or *Microccus luteus* (IFO 3067 and IFO 12708).

10 Claims, No Drawings

METHOD FOR THE PRODUCTION OF TREHALOSE USING STRAINS OF MICROCOCCUS AND DEINOCOCCUS

FIELD OF THE INVENTION

This invention relates to a method for the production of trehalose (O-α-D-glucopyranosyl-(1→1)-α-D-glucopyranoside).

PRIOR ART

Trehalose is omnipresent in the natural kingdom, e.g. in microorganisms, algae, plants and animals (insects), and is known to be playing the role of an energy reserve for these living things. Recently discovered is the function of trehalose to protect cells and intracellular polymers from freezing or dehydration, which has led to the application of trehalose as a preservative in a variety of products such as foods, pharmaceutical preparations, cosmetic products and so on. It is, therefore, of great industrial significance to produce trehalose at low cost on a mass production scale.

The known technology for the production of trehalose includes an extractive process starting with baker's yeast (J. Amer. Chem. Soc. 72, 2059, 1950), a process using an ascomycotinous yeast of the genus Hansenula (German Patent No.266884), and an extractive process starting with a fungus of the genus Rhizoctonia or Sclerotium (Japanese Patent Application Laid-open No. 3-130084, EP-5169767).

Regarding the technology for extracellular accumulation of trehalose, it has been reported that *Arthrobacter paraffineus* (Agr. Biol. Chem. 33, 190,1969), *Nocardia uniformis* (Japanese Patent Application Laid-open No. 50-154485), and bacteria of the genus Brevibacterium, the genus Corynebacterium, the genus Microbacterium and the genus Arthrobacter (Japanese Patent Application Laid-open No. 5-211882, EP-555540) elaborate and accumulate trehalose in culture medium.

However, in the above extractive processes for extracting trehalose from the microbial cell, the yield of trehalose per unit amount of culture medium depends upon the quantity of grown cells.

Moreover, in the technology for extracellular accumulation of trehalose, the concentration of trehalose in culture medium is low, or the carbon sources employed are limited, or the osmotic pressure must be maintained at a high level.

SUMMARY OF THE INVENTION

The present invention is directed to a process for producing trehalose, which comprises growing a strain of microorganism belonging to Gram-positive cocci having not less than about 55 mol % G+C (guanine and cytosine) of the DNA and having the ability to produce and extracellularly accumulate trehalose in the culture medium.

And the present invention is directed to an isolated and biologically pure culture of *Micrococcus varians* No. 39, which requires thiamine, p-aminobenzoic acid, nicotinamide and biotin simultaneously for its growth.

The microorganism for use in this invention may be any strain of microorganism belonging to the Gram-positive cocci having not less than about 55 mol % G+C of DNA and capable of producing trehalose extracellularly. The strain may be a known strain or a new strain isolated from the soil, plant or other source only if it belongs to the Gram-positive cocci having not less than about 55 mol % G+C of DNA and has the ability to extracellularly produce trehalose.

As said microorganism, the strains of the genus Micrococcus or of the genus Deinococcus are preferable. As the microorganism of the genus Micrococcus, the strains of the species *Micrococcus varians* are preferable. As the microorganism of the genus Deinococcus, the strains of the species *Deinococcus proteolyticus* are preferable.

Preferred examples of such strain of the genus Micrococcus include *Micrococcus agilis* IFO 15323, *Micrococcus luteus* IFO 3067, *Micrococcus luteus* IFO 12708, *Micrococcus varians* IFO 3765 and *Micrococcus varians* No. 39, among others. Particularly, *Micrococcus varians* No. 39 is a useful strain.

Preferred examples of such strain of the genus Deinococcus include *Deinococcus erythromyxa* IFO 15344, *Deinococcus proteolyticus* IFO 15345 and *Deinococcus radiopugnans* IFO 15348. Particularly, *Deinococcus proteolyticus* IFO 15345 is a useful strain.

Of the above mentioned strains, *Micrococcus agilis* IFO 15323, *Deinococcus erythromyxa* IFO 15344, *Deinococcus proteolyticus* IFO 15345 and *Deinococcus radiopugnans* IFO 15348 have been listed in Institute for Fermentation, Osaka(IFO), Research Communications, 1993, and *Micrococcus luteus* IFO 3067, *Micrococcus luteus* IFO 12708 and *Micrococcus varians* IFO 3765 have been listed in Institute for Fermentation, Osaka(IFO). List of Cultures, 1992, ninth edition. Said microorganisms are available from the Institute for Fermentation, Osaka, Japan.

Among the above strains, *Micrococcus varians* No. 39 is a novel trehalose-producing strain isolated from soil and has the bacteriological characteristics shown in Table 1.

TABLE I

Taxonomical characteristics of the trehalose-producing *Micrococcus varians* No. 39:

| Characteristics | Strain No. 39 |
| --- | --- |
| Gram staining | + |
| Morphology | Cocci |
| Cell size | 0.9–1.0 μm |
| Motility | − |
| Color of cells | Slightly yellowish |
| Catalase | + |
| Oxidase | − |
| Cellular fatty acids | anteiso − 15:0 + anteiso − 17:0 (No hydroxy acids) |
| Amino acids of peptidoglycan | Glu:Lys:Ala = 1.00:0.97:5.80 |
| (Peptidoglycan type) | L-Lys-L-Ala$_{3-4}$ (A3α,A11.7) |
| Menaquinone | MK-7(H$_2$) |
| Mol % G + C of DNA | 69.9 |
| Urease | + |
| β-galactosidase | + |
| Phosphatase | − |
| Arginine dihydrolase | − |
| Acetoin | − |
| Nitrate reduction | + |
| Hydrolysis of | |
| Gelatin | + |
| Starch | − |
| Esculin | − |
| Polyoxyethylenesorbitanmonooleate | − |
| Growth on Simmon's citrate agar | + |
| Growth on inorganic nitrogen agar | − |
| Acid production from | |
| D-Glucose | + |
| D-Fructose | + |

TABLE I-continued

Taxonomical characteristics of the trehalose-producing *Micrococcus varians* No. 39:

| Characteristics | Strain No. 39 |
|---|---|
| D-Galactose | + |
| D-Mannose | − |
| D-Xylose | + |
| D-Rhamnose | − |
| Maltose | + |
| Lactose | − |
| Sucrose | + |
| Trehalose | + |
| Glycerol | − |
| Sorbitol | − |
| Temp. range for growth (°C.) | 20–37° C. |
| Optimum temp. (°C.) | 30° C. |
| Strict aerobes | + |
| Growth on nutrient agar with 10% NaCl | + |
| Growth on nutrient agar with 15% NaCl | − |
| Lysozyme susceptibility (400 μg/ml) | Resistant |
| Lysozyme susceptibility (800 μg/ml) | Sensitive |

Comparison of the nutrient requirement, between said *Micrococcus varians* No. 39 and the other *Micrococcus varians* strains, i.e. *Micrococcus varians* IFO 3765 and IFO 15358, are shown in Table 2. *Micrococcus varians* IFO 15358 is listed in Research Communication, 1993 of the Institute for Fermentstion, Osaka, Japan.

TABLE 2

| Omitted component | Growth | | |
|---|---|---|---|
| | *M. varians* No. 39 | *M. varians* IFO 3765 | *M. varians* IFO 15358 |
| Casamino acid | + | + | − |
| Nucleotide base mixture | + | + | + |
| Vitamin mixture | − | − | − |
| Thiamine.HCl | − | − | − |
| Riboflavin | + | + | + |
| Ca-pantothenate | + | + | + |
| Vitamin B₆ | + | + | + |
| Vitamin B₁₂ | + | + | + |
| Biotin | − | + | + |
| Folic acid | + | + | + |
| p-Aminobenzoic acid | − | + | + |
| Nicotinamide | − | + | − |
| Inositol | + | + | + |
| Control (complete medium) | + | + | + |

+, growth
−, no growth

In the Table 2, the cases other than control demonstrate the results of the growth of the bacteria in the complete medium in which the substance is respectively omitted.

The details of casamino acid (A), nucleotide base mixture (B) and vitamin mixture (C) in tables are shown below:

(A) Casamino acid: Bact casamino acid, vitamin test; DIFCO Lab. USA.
(B) Nucleotide base mixture: adenine, guanine, cytosine, thymine and uracil.
(C) Vitamin mixture: thiamine, riboflavin, Ca-pantothenate, vitamin B₆, vitamin B₁₂, biotin, folic acid, p-aminobenzoic acid, nicotinamide and inositol.

The composition of complete medium is shown in Table 3.

TABLE 3

Composition of complete medium

| | | |
|---|---|---|
| Glucose | 20 | g/l |
| (NH₄)₂HPO₄ | 2 | |
| K₂HPO₄ | 4 | |
| MgSO₄.7H₂O | 4 | |
| CaCl₂.2H₂O | 0.01 | |
| MnSO₄.4~6H₂O | 0.01 | |
| NaCl | 0.01 | |
| FeCl₃.6H₂O | 0.01 | |
| H₃BO₄ | 0.001 | |
| Na₂MoO₄.2H₂O | 0.002 | |
| CuSO₄.5H₂O | 0.005 | |
| ZnCl₂ | 0.007 | |
| Casamino acid | 6 | |
| Adenine | 10 | mg/l |
| Guanine | 10 | |
| Cytosine | 10 | |
| Thymine | 10 | |
| Uracil | 10 | |
| Thiamine.HCl | 400 | μg/l |
| Riboflavin | 400 | |
| Ca-pantothenate | 400 | |
| Vitamin B₆ | 400 | |
| Vitamin B₁₂ | 400 | |
| Biotin | 10 | |
| Folic acid | 10 | |
| p-Aminobenzoic acid | 200 | |
| Nicotinamide | 400 | |
| Inositol | 2000 | |

As is clear from Table 2, the strain No. 39 requires thiamine, p-aminobenzoic acid, nicotinamide and biotin simultaneously for its growth.

Comparison of the above characteristics of this trehalose producer strain No. 39 with relevant descriptions in Bergey's Manual of Systematic Bacteriology 1986 revealed that the strain No.39 is a new strain belonging to the species *Micrococcus varians*. This microorganism has been deposited with Institute for Fermentation, Osaka (IFO), Japan under the accession number of IFO 15442 as of February 26, 1993, and with National Institute of Bioscience and Human-Technology(NIBH), Agency of Industrial Science and Technology, the Ministry of International Trade and Industry, Japan, having an address which is 1-3, Higashi 1-chome Tsukuba-shi, Ibaraki-ken 305, Japan, under the accession number of FERM BP-4238 under the Budapest Treaty as of March 10, 1993.

It should be understood that any strain derived from the above strain by artificial mutation can also be used in the production process of this invention insofar as it belongs to the Gram-positive cocci having not less than about 55 mol % of G+C of DNA and has the ability to produce and extracellularly accumulate trehalose in the medium. The mol % of G+C of the DNA is up to 75%.

In the present process, suitable strains are those having a conversion of the yield of trehalose from a carbon source is not less than about 30%. The conversion yield is up to about 70%.

In practicing the process of this invention, the above strain of microorganism is first Cultivated in a culture medium. This cultivation can be carried out under aerobic conditions by the conventional shaking culture, submerged aerobic culture or other method in a batch, fed-batch or continuous culture. The medium can be of the ordinary composition which permits a sustained growth of the bacteria. Thus, various carbon and nitrogen sources can be selectively employed. In addition, essential growth factors and growth promotors such as inorganic salts, amino acids and vitamins are preferably added. The carbon source which can be employed includes various saccharides such as glucose, fructose, raw sugar, molasses, etc., sugar alcohols such as glycerol, sorbitol, etc. and various organic acids and these sources of carbon can be used singly or in combination. These carbon sources may be added to the medium at initiation at necessary concentrations or added intermittently in the course of cultivation.

Examples of nitrogen sources include various organic nitrogen sources such as peptone, soybean flour, corn steep liquor, yeast extract, meat extract, urea, etc. and inorganic nitrogen sources such as ammonium salts of sulfuric acid, nitric acid, hydrochloric acid, carbonic acid, phosphoric acid, etc., aqueous ammonia, ammonia gas, etc. These sources of nitrogen can be used alone or in combination.

Examples of inorganic salts include the sulfates, hydrochlorides, carbonates, nitrates, phosphates, acetates, etc. of calcium, potassium, sodium, magnesium, manganese, iron, copper, zinc, etc. and these salts can be used singly or in suitable combinations as necessary.

Since the bacteria for use in this invention require for growth one or more vitamins such as nicotinamide, thiamine, biotin, p-aminobenzoic acid, etc., such vitamins are essential constituents of the medium. To fulfill this need, such vitamins or vitamin derivatives, microbial cells or extracts containing such vitamins and/or naturally-occurring organic materials such as meat extract and the like are added. Aside from the forgoing, for the purpose of promoting growth of the bacteria used, various other vitamins and amino acids may be added whenever required. Medium components and their concentrations favoring the growth of the bacteria used which contribute to the production of trehalose are selected. Moreover, for defoaming purposes, an antifoaming agent such as silicone oil can be advantageously added to the medium at initiation of cultivation or in the course of cultivation.

Generally, the pH of the medium is preferably maintained in the range of about 4 to 9 and more preferably between about 5 and 8. In order to maintain this range, phosphate buffer or calcium carbonate may be added to the medium beforehand or the pH may be corrected in the course of cultivation, by adding alkali hydroxide, aqueous ammonia, ammonia gas or the like when the medium pH has dropped below the threshold level or conversely by adding a mineral acid, e.g. hydrochloric acid or sulfuric acid, or an organic acid, e.g. acetic acid or citric acid, when the pH has risen beyond the upper limit of said range.

The incubation temperature is selected from the range of about 20° to 40° C. and should be the optimal temperature for growth of the strain used and extracellular accumulation of trehalose.

The incubation time should be such that the accumulation of trehalose per unit volume of medium will be maximal and this requirement is met generally in about 2 days to 2 weeks.

After cultivation under the above conditions, the trehalose produced in the culture broth can be easily recovered and isolated by a combination of the known harvesting procedures and purification procedures such as chromatography, crystallization, etc. Thus, separation of the cells from the final culture broth can be accomplished by centrifugation, by filtration with a filter press or a ceramic filter or by ultrafiltration. The supernatant fluid thus obtained is concentrated as necessary and subjected to column chromatography using activated charcoal or a cation and/or anion exchange resin to collect the trehalose fractions. This eluate is concentrated to a trehalose concentration of about 40 to 60 w/v % and utilizing the dependency of the solubility of trehalose on the concentration of ethanol, crystallization is carried out by adding ethanol to a final concentration of about 70 to 90 v/v %. This crystallization can also be carried out from water by utilizing the temperature dependence of the solubility of trehalose. When the resulting crude crystals are qualitatively inadequate, the crude crystals may be redissolved in water for recrystallization to provide pure crystals. In this manner, white crystals of trehalose dihydrate can be obtained.

By the process of this invention, trehalose can be produced with improved efficiency. Thus, because the rate of conversion from the carbon source to trehalose is high, the accumulation yield of trehalose per unit volume of culture medium is remarkably enhanced. Thus, trehalose can be produced commercially on a mass production scale. Furthermore, since the process of this invention allows trehalose to be accumulated in high concentration in the medium, the product trehalose can be easily recovered and purified.

The trehalose thus produced can be utilized in the known applications, e.g. as a sweetener and preservative in foods, as a humectant in cosmetic products, a protectant in peptide preparations, a stabilizer in liposome preparations, or a protective agent in blood preparations. To cite an example, the trehalose can be utilized for protecting foods from dehydrative degradation in the high-temperature environment by adding it at the level of 0.5 to 15% (Japanese Patent Application Laid-open No. 2-503864, GB-2206273).

By the process of this invention, trehalose can be accumulated in high concentration in the culture supernatant. Therefore, the separation and purification of trehalose are facilitated.

Thus, the method of this invention provides for an efficient production of the industrially useful trehalose on a commercial scale.

The following examples are intended to describe this invention in further detail and should by no means be construed as limiting the scope of the invention.

EXAMPLE 1

A soil sample, 0.5 g, obtained in Tsukuba City, Ibaraki Prefecture, Japan was suspended in 2 ml of sterilized physiological saline and after appropriate dilution, 0.1 ml was inoculated on P agar plates (Bacto Peptone (DIFCO) 1.0 w/v %, yeast extract 0.5 w/v %, sodium chloride 7.5 w/v %, glucose 0.1 w/v % and agar 1.5 w/v % ). These agar plates were incubated at 32° for 3 days and the resulting colonies were morphologically studied using a microscope. About 200 strains of the coccal organism giving light yellow to yellow colonies were picked and inoculated on agar slants (Trypticase soy broth (BBL Microbiology Systems: Berton Dickinson and Company, USA) 3.0 w/v %, glucose 1.0 w/v % and agar 2.0 w/v % ).

Then, one loopful of each on the above agar slants was transferred to 200 ml conical flasks each containing 30 ml of fermentation medium A shown in Table 4 of the following Example 2 and incubated at 32° C. for 3 days. The resulting culture broth was centrifuged to separate the cells and the supernatant was analyzed by high-performance liquid chromatography (column: Shodex Sugar SZ5532 (Showa Denko K. K., Japan), eluent:acetonitrile-water=80:20 (v/v), flow rate: 1 ml/min., temperature: 50° C., detector: differential refractometer). One strain was selected that produced an oligosaccharide having the same retention time as that of Sigma's trehalose used as the standard. This strain was identified to be a microorganism belonging to the *Micrococcus varians* by reference to Bergey's Manual of Systematic Bacteriology. This strain was accordingly named Micrococcus varians No. 39.

EXAMPLE 2

Conical flasks, of 200 ml capacity, each containing 20 ml of seed medium A, shown in Table 4, were respectively inoculated with one loopful of *Micrococcus agilis* IFO 15323, *Micrococcus luteus* IFO 3067, *Micrococcus luteus* IFO 1270 8, *Micrococcus varians* IFO 3765 or *Micrococcus varians* No. 39 (IFO 15442, FERM BP-4238), grown on agar slants (Trypticase soy broth 3.0 w/v %, glucose 1.0 w/v % and agar 2.0 w/v %), and each flask was incubated at 32° C. on a rotary shaker for 18 hours. However, Micrococcus agilis IFO 15323 was cultivated at 24°. The results are shown in Table 4.

TABLE 4

| Medium composition | Seed medium A | Seed medium B | Fermentation medium A | Fermentation medium B | Fermentation medium C |
|---|---|---|---|---|---|
| Glucose[1] | 10.0 g/l | 20.0 g/l | 30.0 g/l | 15.0 g/l | 30.0 g/l |
| Glycerol | | | | 15.0 | |
| TSB[2] | 30.0 | | | | |
| Yeast extract | | | 6.0 | | |
| CSL[3] | | 20.0 | | 8.0 | 10.0 |
| Urea | | 3.0 | | | |
| (NH4)2HPO4 | | | | 1.0 | 1.5 |
| KH2PO4 | | 1.0 | 4.0 | | 1.0 |
| K2HPO4 | | | | 2.0 | |
| MgSO4.7H2O | | 0.5 | 4.0 | 4.0 | 0.5 |
| CaCl2.2H2O | | 1.0 | 0.01 | 0.01 | 0.01 |
| MnSO4.4–6H2O | | | 0.01 | 0.01 | 0.01 |
| FeSO4.7H2O | | 1.0 | 0.01 | 0.01 | 0.01 |
| CuSO4.5H2O | | 0.005 | 0.0002 | 0.0002 | 0.0002 |
| Thiamine hydrochloride | | | | 0.01 | 0.01 |
| Biotin | | | | 0.00001 | 0.00001 |
| Nicotinamide | | | | 0.02 | 0.02 |
| p-Aminobenzoic acid | | | | 0.0002 | 0.0002 |
| CaCO3 | | | | | 5.0 |
| Initial pH | Not corrected | 6.0 | 7.2 | 7.5 | 7.5 |

Note
[1]: Separately sterilized
[2]: Trypticase soy broth
[3]: Corn steep liquor This seed culture, in 1.5 ml portions, was transferred to 200 ml conical flasks each containing 30 ml of fermentation medium A shown above in Table 4 and was incubated on a rotary shaker at 32° C. for 5 days. (*Micrococcus agilis* IFO 15323 was cultivated at 24° C.). After cultivation, the broth (5 ml) was centrifuged (5000×G, 15 min.) to separate the cells and the trehalose content of the supernatant was determined by high-performance liquid chromatography as in Example 1. The results are shown in Table 5.

TABLE 5

| Strain | Trehalose (mg/ml) |
|---|---|
| *Micrococcus agilis* IFO 15323 | 2.28 |
| *Micrococcus luteus* IFO 3067 | 2.31 |
| *Micrococcus luteus* IFO 12708 | 2.29 |
| *Micrococcus varians* IFO 3765 | 2.23 |
| *Micrococcus varians* No. 39 | 10.43 |

In the case of *Micrococcus varians* No. 39, the calculated rate of conversion from carbon source to trehalose was 34%.

EXAMPLE 3

A seed culture of *Micrococcus varians* No. 39 (IFO 15442, FERM BP-4238) was prepared by the procedure described in Example 2. This culture, in 1.5 ml portions, was transferred to 200 ml conical flasks each containing 30 ml of fermentation medium B shown in Table 4 (given in Example 2) and was incubated on a rotary shaker (200 rpm) at 32° C. for four days. After completion of cultivation, trehalose was assayed by the method described in Example 1. As a result, it was found that 16.7 mg/ml of trehalose had been accumulated in the culture supernatant. Based on this result, the trehalose yield (the rate of conversion of the carbon source used to trehalose) was calculated to be 57 %.

EXAMPLE 4

Conical flasks, of 200 ml capacity, each containing 20 ml of seed medium B shown in Table 4 (given in Example 2) were respectively inoculated with one loopful of *Micrococcus varians* No. 39 (IFO 15442, FERM BP-4238), grown on an agar slant (Trypticase soy broth 3.0 w/v %, glucose 1.0 w/v % and agar 2.0 w/v %), and incubated on a rotary shaker (200 rpm) at 32° C. for 18 hours. This seed culture, in 1.5 ml portions, was transferred to 200 ml conical flasks each containing 30 ml of fermentation medium C shown in Table 4 (given in Example 2) and cultivated on a rotary shaker (200 rpm) at 32° C. On day 2 and day 4 of cultivation, 1.5 ml each of 60% glucose solution was added and the cultivation was continued for a total of 13 days. Then, trehalose in the culture supernatant was assayed by the method described in Example 2. As a result, 36.0 mg/ml of trehalose was found to have been accumulated. The rate of conversion from the carbon source to trehalose was 40%.

EXAMPLE 5

From the final culture broth obtained above in Example 4, trehalose was separated and purified by the following procedure. Thus, 200 ml of the broth was centrifuged (5000×G, 15 min.) to separate the culture supernatant and 180 ml of the supernatant was applied to a column (3×30 cm) of activated charcoal (LH2C carbon, Takeda Chemical Industries, Ltd., Japan). The column was then washed with about 800 ml of distilled water and elution was carried out with 10 v/v % ethanol. The trehalose-containing fractions were pooled (300 ml) and concentrated under reduced pressure to 10 ml. To this concentrate was added ethanol gradually to a final ethanol concentration of 80 v/v % and the mixture was allowed to stand at 4° C. overnight. The resulting crystals were collected by filtration, dissolved in 8 ml of distilled water and the above ethanol treatment was carried out again. The resulting crystals were washed with a small amount of ethanol and dried at 60° C. for 5 hours. In this manner, 4.8 g of white crystals were ultimately obtained. The measured specific rotation of this crystalline product was $[\alpha]_D^{25} = +175.4$ and the thermal differential analysis revealed that the product had a water content of 9.64% and a melting point of 206.7° C. These values were in good agreement with the corresponding values of Sigma (USA)'s trehalose dihydrate (D(+) trehalose dihydrate, crystalline, Product Number T5251) used as the standard. The infrared absorption spectrum of this product was also in good agreement with that of Sigma's trehalose. Based on the above results, this crystalline product was confirmed to be trehalose dihydrate.

EXAMPLE 6

Conical flasks, of 200 ml capacity, each containing 20 ml of seed medium A, shown in Table 4, were respectively inoculated with one loopful of *Deinococcus erythromyxa* IFO 15344, *Deinococcus proteolyticus* IFO 15345 or *Deinococcus radiopugnans* IFO 15348 grown on agar slants (Trypticase soy broth 3.0 w/v %, glucose 1.0 w/v % and agar 2.0 w/v %) and each flask was incubated at 32° C. on a rotary shaker(200 rpm) for 18 hours.

This seed culture, in 1.5 ml portions, was transferred to 200 ml conical flasks each containing 30 ml of fermentation medium A shown above in Table 4 and was incubated on a rotary shaker(200 rpm) at 32° C. for 5 days. After cultivation, the broth (5 ml) was centrifuged (5000×G, 15 min.) to separate the cells and the trehalose content of the supernatant was determined by high-performance liquid chromatography as in Example 1. The results are shown in Table 6.

TABLE 6

| Strain | Trehalose (mg/ml) |
|---|---|
| *Deinococcus erythromyxa* IFO 15344 | 2.05 |
| *Deinococcus proteolyticus* IFO 15345 | 9.34 |
| *Deinococcus radiopugnans* IFO 15348 | 2.84 |

In the case of *Deinococcus proteolyticus* IFO 15345, the calculated rate of conversion from carbon source to trehalose was 31%.

What we claim is:

1. A method for producing trehalose which comprises cultivating a microorganism selected from the group consisting of *Deinococcus proteolyticus*, IFO 15345, *Deinococcus erythromyxa*, IFO 15344, *Deinococcus radiopugnans*, IFO 15348, *Micrococcus varians*, strain No. 39 (FERM BP-4238), *Micrococcus agilis*, IFO 15323, *Micrococcus luteus* IFO 3067, *Micrococcus luteus* IFO 12708 and *Micrococcus varians*, IFO 3765 having the ability to produce and extracellularly accumulate trehalose in a culture medium, and harvesting trehalose from the culture medium.

2. A method for producing trehalose, which comprises cultivating *Micrococcus varians* strain No. 39 (FERM BP-4238), having the ability to produce and extracellularly accumulate trehalose in a culture medium, and harvesting trehalose from the culture medium.

3. The method as claimed in claim 2, wherein the strain converts at least 30% of the carbon source in the medium to trehalose.

4. The method for producing trehalose of claim 1, wherein said microorganism is *Deinococcus proteolyticus*, IFO 15345.

5. The method for producing trehalose of claim 1, wherein said microorganism is *Deinococcus erythromyxa*, IFO 15344.

6. The method for producing trehalose of claim 1, wherein said microorganism is *Deinococcus radiopugnans*, IFO 15348.

7. The method for producing trehalose of claim 1, wherein said microorganism is *Micrococcus agilis*, IFO 15323.

8. The method for producing trehalose of claim 1, wherein said microorganism is *Micrococcus luteus* IFO 3067.

9. The method for producing trehalose of claim 1, wherein said microorganism is *Micrococcus luteus* IFO 12708.

10. The method for producing trehalose of claim 1, wherein said microorganism is *Micrococcus varians*, IFO 3765.

* * * * *